United States Patent [19]

Ashton et al.

[11] 4,406,902

[45] Sep. 27, 1983

[54] DIPEPTIDASE INHIBITORS

[75] Inventors: Wallace T. Ashton, Clark; Louis Barash, Westfield; Jeannette E. Brown, Summit; Donald W. Graham, Mountainside, all of N.J.

[73] Assignee: Merck & Co., Inc., Rahway, N.J.

[21] Appl. No.: 285,161

[22] Filed: Jul. 23, 1981

Related U.S. Application Data

[63] Continuation-in-part of Ser. No. 187,930, Sep. 17, 1980, abandoned.

[51] Int. Cl.$^3$ ............................................ C07D 213/70
[52] U.S. Cl. ................................. 424/251; 260/402.5; 424/263; 424/266; 424/269; 424/270; 424/273 R; 424/273 N; 424/271; 424/274; 424/305; 424/309; 424/317; 424/318; 424/319; 542/416; 560/17; 560/18; 562/431

[58] Field of Search .................... 542/416; 560/17, 18; 562/431; 260/402.5; 424/251, 263, 266, 273, 270, 269, 274, 271, 305, 309, 317, 318, 319

[56] References Cited

U.S. PATENT DOCUMENTS 4,232,036 11/1980 Christensen .......................... 542/416

Primary Examiner—Arthur P. Demers
Attorney, Agent, or Firm—Daniel T. Szura; Donald J. Perrella; Hesna J. Pfeiffer

[57] ABSTRACT

Novel chemical compounds are provided which selectively inhibit the metabolism of dipeptidase (E.C.3.4.13.11) and therefore are useful in combination with antibacterial products. These chemical compounds are Z-2-(2,2-dimethylcyclo-propanecarboxamido)-ω-pyridylthio-2-alkenoic acids (and related arylthio and heterocyclylthio analogs).

12 Claims, No Drawings

DIPEPTIDASE INHIBITORS

RELATED APPLICATION

This application is a continuation-in-part of our copending application Ser. No. 187,930, filed Sept. 17, 1980, now abandoned.

INTRODUCTION

A new class of fused ring β-lactam antibiotics, including thienamycin and its semisynthetic derivatives, epithienamycins, and olivanic acids, has recently been described. These compounds which will be defined more extensively below, are hereinafter referred to as the "thienamycin class of compounds". These compounds have a high level of antibacterial activity, but are subject to extensive metabolism by mammalian species.

The kidney was identified as the primary site of metabolism, and an enzyme was purified from renal extracts which catalyzed the inactivation of thienamycin by hydrolysis of the β-lactam. By such criteria as cytological localization, substrate specificity and susceptibility to enzyme inhibitors, this enzyme is very similar if not identical to a widely studied renal dipeptidase (E.C.3.4.13.11), also referred to in the literature as "dehydropeptidase I". However, the β-lactamase activity is exhibited only toward the thienamycin class of compounds. Indeed, there exists no precedent example of the mammalian metabolism via β-lactam cleavage of any representative of the classical β-lactam antibiotics, the penicillins and cephalosporins.

DETAILED DESCRIPTION OF THE INVENTION

The chemical substances which selectively inhibit the metabolism of the dipeptidase [E.C.3.4.13.11], also called "dipeptidase inhibitors", include chemical compounds which are substituted 2-alkenoic acids having the following formula

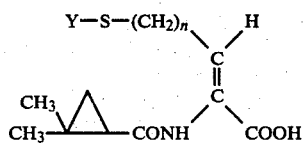

wherein n is an integer from 3-5 and Y is a heterocyclic or phenyl group which may be substituted or unsubstituted and the loweralkyl ($C_{1-6}$) esters and pharmaceutically acceptable salts thereof.

By the term "heterocyclic" is meant pyridyl, pyrimidinyl, tetrazolyl, imidazolyl, thiadiazolyl, thiazolinyl, and the like. These rings, and the phenyl ring can be unsubstituted or substituted with hydroxyl, oxo, carbonyl, or methyl. Y-groups include 2-pyridyl; 4-pyridyl; 3-hydroxy-2-pyridyl; 3-carboxy-2-pyridyl; 5-carboxy-2-pyridyl; 2-carboxyphenyl; 1-methyl-1,2,3,4-tetrazol-5-yl; 4-carboxy-6-hydroxy-2-pyrimidinyl; and others.

The preferred configuration at the cyclopropyl center is S, although the R,S mixture has been prepared and is active.

The most active compounds are those in which n is 4, and Y is 3-carboxy-2-pyridyl, or 3-hydroxy-2-pyridyl, in the S-form.

The Z configuration (J. E. Blackwood et al., J. Am. Chem. Soc., 90, p. 509 (1968)) is assigned to the above compounds on the basis of their NMR spectra by analogy with the work of A. Srinavasan et al. Tetrahedron Letters, 891 (1976).

Although these compounds of Formula I, when $R^1$ is H, are described and named as the free acids, it will be apparent to one skilled in the art that various pharmaceutically acceptable derivatives such as alkali and alkaline earth metal, ammonium, or amine salts, or the like can be employed as equivalents thereto. Salts such as the sodium, potassium, calcium, or tetramethylammonium salts are suitable.

UTILITY OF THE INVENTION

As noted above, the compounds of this invention are dipeptidase (E.C.3.4.13.11) inhibitors, and can be used in combination with antibacterial compounds which are subject to renal degradation. The group of antibiotics of present primary importance for use in combination with the Z-2-acylamino-3-mono-substituted propenoates of this invention are the "thienamycin class of compounds".

The term "thienamycin class of compounds" is used to identify any of a number of naturally occurring, semi-synthetic, or synthetic derivatives or analog compounds having a common fused-ring β-lactam nucleus. These compounds can be generically classed as 6- and (optionally) 2-substituted pen-2-em-3-carboxylic acids and 1-carbadethia-pen-2-em-3-carboxylic acids or 1-azabicyclo[3.2.01]hept-2-ene-7-one-2-carboxylic acids.

Specific compounds particularly useful in this invention are represented structurally in the following formula II:

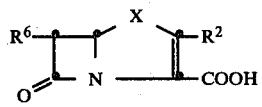

wherein X can be $CH_2$ or S; $R^2$ can be hydrogen; S-alkyl wherein the alkyl group is from 1 to 6 carbons; $SCH_2CH_2NHR^3$, wherein $R^3$ is hydrogen, acetyl, formimidoyl, acetimidoyl;

—S(O)—CH=CHNHCOCH$_3$ and

—S—CH=CHNHCOCH$_3$; and $R^6$ is $\underset{R^7}{CHCH_3}$ wherein $R^7$ is hydrogen, hydroxy or sulfonyloxy, or $R^6$ is H. All possible stereoisomeric forms are included within the above structural definition.

All of these compounds within Formula II are described in the literature. When X is $CH_2$, and R is $SCH_2CH_2NH_2$, and $R^6$ is $CH(OH)CH_3$, the compound is known as thienamycin, an antibiotic produced by fermentation of S. cattleya, described and claimed in U.S. Pat. No. 3,950,357, issued Apr. 13, 1976. The N-substituted derivatives of thienamycin, i.e., in the formula II above wherein R is other than hydrogen, are disclosed and claimed in co-pending U.S. applications and their published foreign equivalents. The fermentation product N-acetyl thienamycin ($R^6$ is $CH(OH)CH_3$, and $R^3$ is acetyl), also called 924A, is claimed in Belgian Pat. No. 848,346, issued May 16, 1977. The N-imidoyl derivatives are covered in Belgian Pat. No. 848,545, issued May 20, 1977. The unsaturated side chain-containing compound, also called N-acetyl-dehydrothienamycin or 924A$_5$ is a fermentation product claimed in U.S. Pat. No. 4,162,323 and also in Belgian Pat. No. 866,035, issued Oct. 17, 1978. Epimeric forms of N-acetyl thienamycin, also called 890A$_1$ and 890A$_3$, as well as the desacetyl 890A$_1$ and desacetyl 890A$_3$ are disclosed, respectively in published French Pat. No. 76 34887, issued Apr. 25, 1980 claiming priority of U.S. Ser. No. 634,300, filed Nov. 21, 1975, and Belgian Pat. No. 848,349, issued May 16, 1977. Epimeric forms forms of the unsaturated thienamycin, also called 890A$_2$ and 890A$_5$ are claimed in published French Pat. No. 77 11891 granted Apr. 20, 1977 claiming priority of U.S. Ser. No. 680,331 filed Apr. 28, 1976. The 6-sulfonyloxycontaining N-acetyl compounds, also called 890A$_9$ or 890A$_{10}$, are claimed respectively, in published French Pat. No. 77 34456, granted June 23, 1980 claiming priority of U.S. Ser. No. 742,957 filed Nov. 17, 1976, and published French Pat. No. 77 34457, granted Mar. 3, 1980, claiming priority of U.S. Ser. No. 742,958 filed Nov. 17, 1976. Desacetyl analogues of 890A$_9$ and 890A$_{10}$ are respectively claimed in U.S. Ser. No. 767,723, filed Feb. 11, 1977, now abandoned, and its continuation U.S. Ser. No. 860,665, filed Dec. 15, 1977, now abandoned, and also in French Pat. No. 78 03666 granted May 5, 1978; and U.S. Ser. No. 767,920, filed Feb. 11, 1977, now abandoned, and its continuation U.S. Ser. No. 006,959, filed Jan. 15, 1979, now abandoned, and also in French patent application No. 78 03667, filed Feb. 9, 1978. Some of these latter compounds in the 890A$_9$ and 890A$_{10}$ series are also known as derivatives of olivanic acid (see Corbett et al., J. Chem. Soc. Chem. Commun. 1977, No. 24, pp. 953–54). Compounds of the Formula I above when R$^2$ is hydrogen, also called descysteaminyl thienamycins, are claimed in U.S. Ser. No. 668,898, filed Mar. 22, 1976, now abandoned, and its continuation-in-part, U.S. Ser. No. 847,297, filed Oct. 31, 1977, now abandoned, and also in Belgian Pat. No. 867,227, granted Nov. 20, 1978.

When R$^6$ is hydrogen, and X is CH$_2$, these compounds are disclosed in U.S. Ser. No. 843,171, filed Oct. 19, 1977, and in Belgian Pat. No. 860,962 granted May 18, 1978.

A thienamycin type antibiotic in which R$^2$ is SCH$_2$CH$_2$NHAc and R$^6$ is C$_2$H$_5$, has been named PS5 and is reported by K. Okaimura et al., J. Antibiotics 31 p. 480 (1978), see also Belgian Pat. No. 865,578.

The compounds in which X is S, also called "penems", are described by R. B. Woodward in "Recent Advances in the Chemistry of β-Lactam Antibiotics", J. Elks (Ed), The Chemical Society, London, 1977, p. 167; R. B. Woodward, Abstracts of Uppsala University 500 Years Symposium on Current Topics in Drug Research, Uppsala, Sweden, October 1921, 1977. Acta. Pharm. Suecica, Vol. 14, Supplement, p. 23, and U.S. Pat. Nos. 4,070,477, issued Jan. 24, 1978 and 4,260,618 issued Apr. 7, 1981, and in British Patent application Nos. 2,013,674 published Aug. 15, 1979 and 2,042,520 published Sept. 24, 1980. The compounds wherein X is S are not limited to those encompassed by formula I above but include, in addition, all of the compounds disclosed in the references listed in this paragraph.

The disclosures of the foregoing patents, pending and abandoned patent applications and literature references are hereby incorporated by reference.

Particularly preferred members within the thienamycin class of compounds are the N-formimidoyl and N-acetamidoyl derivatives of thienamycin. The crystalline form of N-formimidoyl thienamycin, which has recently been described, is also useful in the practice of this invention. An example illustrating a preferred way of making this compound follows:

ILLUSTRATIVE EXAMPLE

N-Formimidoyl thienamycin, (NFT) crystalline

Step A. Benzylformimidate hydrochloride

A 3 l. three-necked flask fitted with an addition funnel, overhead stirrer, and a reflux condenser, was charged with a mixture of benzyl alcohol (125 g., 1.15 mol) formamide (51 g., 1.12 mol) and anhydrous ether (1200 ml.). The mixture was stirred vigorously at room temperature (20°–25° C.) under a nitrogen atmosphere and benzoyl chloride (157 g., 1.12 mol) in 50 ml. of anhydrous ether was added dropwise using the addition funnel. The addition required approximately 50 minutes.

The reaction mixture was stirred an additional 60 minutes at room temperature. The ether was removed by decantation and 300 ml. of acetic anhydride in 500 ml. of anhydrous ether was added. The mixture was stirred 30 minutes at room temperature. The precipitate was allowed to settle and the ether-acetic anhydride was again removed by decantation. The solid was collected by filtration, washed with 500 ml. of ether and dried in vacuo over KOH at 25° C. for 2 hours to give 130 g. (67%) of benzylformimidate hydrochloride as a white solid.

The product was assayed by NMR δ (DMSO) 5.7 (s, 2H, φCH$_2$), 7.5 (s, 5H, φ), 9.0 (s, 1H HC=N). The product is thermally unstable. It decomposes to formamide and benzyl chloride at 0° C. and above. However, no appreciable decomposition was detected on storage at −20° C. for 2 months.

Step B. Derivatization of Thienamycin

Thienamycin (in the form of a 6 l. aqueous solution, pH=6.5, concentrate from the fermentation broth, containing 28 g. thienamycin) was placed in a large beaker (12 l) and cooled to 0° C. The beaker was equipped with a pH meter and an efficient high speed stirrer. The pH was raised to 8.5 by the careful addition of 3 N KOH (KOH was added dropwise via syringe to the stirred solution). The solution was treated with 6 equivalents of solid benzyl formimidate hydrochloride (~100 g.) in portions while maintaining the pH at 8.5±0.3 by the addition of 3 N KOH (200 ml.) using a syringe. The addition required 3–5 min. The reaction mixture was stirred for 6 min. at 0° C. and then assayed by liquid chromatography to insure completion of the reaction. The solution was adjusted to pH 7 with 1 N HCl. The volume of the reaction mixture was measured, and the solution was assayed by UV. The neutralized reaction mixture was concentrated to 15 g./l. on the reverse osmosis unit at <10° C. The volume of the concentrate was measured and the pH was adjusted to 7.2–7.4, if necessary. The concentrate was filtered through a medium porosity sintered glass funnel to remove any solids present after concentration.

Step C. Dowex 50W×2 Chromatography

The concentrate (750–1000 ml., 15–20 g.) was applied to 0° C. to a precooled 18 l. column of Dowex 50W×2 in the potassium cycle (200–400 mesh resin) and the column was eluted at 0°–5° C. with distilled deionized water a flow rate of 90 ml/min. and a head pressure of 0-45 psig.

Forerun fractions of 4 l., 2 l., and one l., were collected followed by 18 fractions of 450 ml. each, and one final fraction of 2 l. Each fraction was assayed by UV (1/100 dilution, NH₂OH extinction was omitted) and the total amount of NFT present in each fraction was calculated. The beginning and end fractions were assayed for liquid chromatography purity and the desired rich cut fractions were combined. The pH of the combined rich cuts was determined by both pH meter and bromothymol blue indicating solutions and was adjusted to pH 7.2-7.4 if necessary. The combined rich cuts (3-4 l.) were then assayed by UV and the total formamidine content was determined, 15-16 g., 75% yield from the column. The rich cuts were concentrated on the reverse osmosis unit at <10° C. as far as possible, then the concentration to 33 g./l. was completed on the circulatory evaporator at less than 28° C. A total volume of about 500 ml. concentrate was obtained.

Step D. Crystallization of N-Formimidoyl Thienamycin

The concentrate from the previous step is adjusted to 7.3, if necessary, and N-formimidoyl thienamycin content assayed by UV, was about 85-90%. The concentrate was filtered through a sintered glass funnel (medium porosity) into a large Erlenmeyer flask. Five volumes (~2200 ml.) of 3A ethanol was filtered into the concentrate and the solution was stirred at room temperature for 10 minutes and at 0° C. for 12-24 hrs.

The crystals were filtered by suction filtration and washed with 0.1 volume (~250 ml.) of 0° C. 80% 3A ethanol followed by 1/25 volume (100 ml.) of 3A ethanol at room temperature. The crystals were dried in vacuo for 12-24 hrs. to give approximately a 40% overall yield of N-formimidoyl thienamycin (10-12 g.).

Analytical results on a 50 g. blend of N-formimidoyl thienamycin, prepared as above, are as follows:

C, theory 45.42%; found, 45.82% H, theory 6.03%; found, 5.72% N, theory 13.24%; found, 13.10% S, theory 10.10%; found, 10.14% residue on ignition, predicted 0.5, found 0.47%;

$[\alpha]_D^{25} = 89.4°$, T.G. = 6.8%, UV $\lambda$max 300 MM, E% = 328.

METHODS OF USING THE INVENTION

As mentioned above, the thienamycintype compound is used in combination with the dipeptidase inhibitor.

The combination of the novel chemical inhibitors of this invention and the thienamycin class compound can be in the form of a pharmaceutical composition containing the two compounds in a pharmaceutically acceptable carrier. The two can be employed in amounts so that the weight ratio of the thienamycin class compound to inhibitor is 1:3 to 30:1, and preferably 1:1 to 5:1.

The components can also be separately administered. For instance, the thienamycin class compound can be administered intramuscularly or intravenously in amounts of 1-100 mg/kg/day, preferably 1-20 mg/kg/day, or 1-5 mg/kg/day, in divided dosage forms, e.g., three or four times a day. The inhibitor can be separately administered, orally, intramuscularly, or IV, in amounts of 1-100 mg/kg/day, or preferably 1-30 mg/kg/day, or 1-5 mg/kg/day. The amounts of the two components administered during one day ideally are within the ratio limits denoted above.

One preferred dosage form known to applicants is as a single dose, of two compounds, one being N-formimidoyl thienamycin and the other being (+)Z-7-(3-carboxy-2-pyridylthio)-2-(2,2-dimethylcyclopropanecarboxamido)-2-heptenoic acid, co-administered in a sterile aqueous IV injection form (sodium salt), at a level of 150 mg. of the thienamycin and either 75 or 150 mg of the heptenoic acid. This dose is given to humans (each assumed to weigh about 80 kg.) from 1 to 4 times a day, or 2-8 mg/kg/day of the thienamycin class compound and 1-8 mg/kg/day of the inhibitor. The thienamycin can also be administered at either 250 or 500 mg., together with the inhibitor at 1:1 (weight) ratio, or 250 or 500 mg also. When this dosage is given 1-4 times daily, from 3.1-25 mg/kg/day is given of each component.

The components, whether administered separately or together are employed in pharmaceutically acceptable carriers such as conventional vehicles adapted for oral administration such as capsules, tablets, or liquid solutions or suspensions. The components separately or together, can also be dissolved in a vehicle adapted for administration by injection. Suitable formulations for oral use, may include diluents, granulating agents, preservatives, binders, flavoring agents, and coating agents. The example of an oral use composition in the combination of active ingredients, or the acid component alone, intermixed in the dry pulverulent state with gelatin, starch, magnesium stearate, and alginic acid, and pressed into a tablet.

As noted above, the presently known preferred method is parenteral administration of the thienamycin class compound and either co-parenteral administration or oral administration of the inhibitor compound.

METHODS OF TESTING THE COMBINATION ANTIBACTERIAL AGENT

As noted, disposition studies with thienamycin, its natural analogs and its semi-synthetic derivatives have revealed a major metabolic degradation pathway of elimination in the various species examined (mouse, rat, dog, chimpanzee, Rhesus monkey). The extent of metabolism is reflected in low urinary recovery and short plasma half-lives. The nature of this degradation was demonstrated to be lactam cleavage by the renal dipeptidase (E.C.3.4.13.11), described first by Bergmann, M. and Schleich, H., Z. Physiol. Chem., 205 65 (1932); see also Greenstein, J. P., Advances in Enzymology, Vol. VIII, Wiley-Interscience, (1948), New York, and Campbell, B. J.; Lin, Y-C., Davis, R. V. and Ballew, E., "The Purification and Properties of Particulate Renal Dipeptidase", Biochim. Biophys. Acta., 118, 371 (1966).

In order to demonstrate the ability of the compounds of Formula I to suppress the action of the renal dipeptidase enzyme, an in vitro screen procedure was followed. This measured the ability of compounds to inhibit hydrolysis of glycyldehydrophenylalanine (GDP) by a solubilized preparation of dipeptidase isolated from hog kidneys. The procedure is as follows: to a 1 ml. system containing 50 mM "MOPS" (3-(N-morpholino)-propanesulfonic acid) buffer, pH 7.1, is added 5 µg of lyophilized enzyme, and the test compound at a final concentration of 0.1 mM. After a five minute incubation at 37° C., GDP is added to a final concentration of 0.05 mM. Incubation is continued for 10 minutes, at 37° C. and hydrolysis of GDP is measured by the change in optical density with time at 275 nm. Inhibition of the enzyme is gauged by comparison to a standard run containing no inhibitor and is expressed as the inhibitor binding constant, $K_i$. This is the concentration of the inhibitor which achieves 50% inhibition of enzyme.

The substrate GDP is employed in preference to thienamycin in this screen because it has a much higher maximal velocity of hydrolysis by renal dipeptidase, thereby reducing the amount of enzyme required. Both GDP and thienamycin have a similar affinity for renal dipeptidase; furthermore, $K_i$'s of inhibitors tested have been identical for the two substrates.

Urinary recovery of thienamycin was measured in all cases with the use of a cylinder or disc diffusion assay, conducted in a manner described in U.S. Pat. No. 3,950,357. This bioassay, with Staphylococcus aureus ATCC 6538 as the test organism, has a useful response range from 0.04 μg/ml to 3.0 μg/ml.

The compounds of this invention are made from an -bromoalkenoic acid.

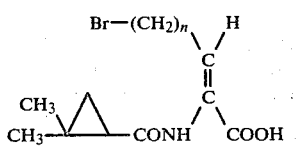

This is condensed with the appropriate mercaptan, YSH, in water in the presence of sodium bicarbonate at ambient temperature. Most of the desired mercaptans are commercially available. Mercapto nicotinic acids can be prepared by reacting chloronicotinic acids with sodium hydrosulfide according to literature methods, see J. Delarge et al., J. Pharm. Belg., 22, 213 (1967); C.A. 68, 59406 (1968); and L. R. Fibel et al., JACS 70, 3908; (1948).

More detail about preparation of the compounds is found in the following examples.

PREPARATIVE EXAMPLE

Z-8-Bromo-2-(2,2-Dimethylcyclopropanecarboxamido)-2-octenoic acid

To a suspension of 14.4 g (0.3 mole) of 50% NaH dispersion in 360 ml of toluene cooled in an ice bath and in a $N_2$ atmosphere was added over 45 minutes a solution of 146 g (0.6 moles) of 1,6-dibromohexane and 57.6 g (0.3 mole) of ethyl 1,3-dithiane-2-carboxylate in 120 ml of DMF. The cooling bath was removed and the mixture stirred at room temperature for 20 hours. The reaction mixture was washed with water (3×210 ml), dried over $MgSO_4$ and evaporated under reduced pressure to give 179.5 g of a yellow oil containing the desired alkylated dithiane, 1,6-dibromohexane and mineral oil. This crude material was used in the next reaction without purification.

To a suspension of 426 g (2.4 moles) of N-bromosuccinamide in 800 ml of acetonitrile and 200 ml of $H_2O$ was added over 45 minutes a solution of the crude dithiane in 100 ml of acetonitrile. The temperature of the reaction mixture was maintained below 25° C. with an ice bath. After stirring at 20° C. for 10 minutes the dark red reaction mixture was poured into 2 l. of hexane-$CH_2Cl_2$ (1:1). The solution was shaken with saturated $NaHSO_3$ (2×400 ml) and water (1×500 ml). Then 400 ml of saturated $Na_2CO_3$ solution was added in small portions (vigorous $CO_2$ solution). After the foaming subsided the funnel was shaken and the aqueous phase separated. The organic layer was extracted with saturated $Na_2CO_3$ solution (400 ml) and water (500 ml) and dried over $MgSO_4$. Removal of the solvent under reduced pressure gave 133.8 g of crude bromo ketoester containing 1,6-dibromohexane and mineral oil. This crude material was used in the next reaction without purification.

A mixture of 133.8 g of crude bromo ketoester, 133 ml of 50% hydrobromic acid and 267 ml of acetic acid was heated at 90° C. (internal temperature) for 75 minutes. The dark solution was evaporated under reduced pressure until most of the acetic acid was removed. The residue was dissolved in 500 ml of ether, washed with water (2×100 ml) and extracted with saturated $NaHCO_3$ (3×200 ml). The combined $NaHCO_3$ extracts were extracted with ether (2×100 ml) and acidified with concentrated HCl. The precipitated oil was extracted with ether (3×200 ml). The ether extracts were washed with water (1×100 ml) and saturated brine (1×100 ml) and dried over $MgSO_4$. Removal of the ether under reduced pressure gave 46.2 g of pure bromo keto acid, homogeneous by TLC (silica gel, 4:1 toluene-acetic acid). The NMR spectrum was consistent with the desired product.

A mixture of 46.1 g (0.194 moles) of the bromo keto acid, 17.6 g (0.156 mole) of 2,2-dimethylcyclopropanecarboxamide and 450 ml of toluene was heated under reflux for 13 hours, with collection of water in a small Dean-Stark trap. After cooling, the clear reaction mixture was extracted with saturated $NaHCO_3$ solution (4×100 ml). The combined extracts were washed with either (2×100 ml) and then the pH was adjusted to 3.5 (pH meter) by addition of concentrated HCl. An oil precipitated which soon crystallized. The solid was filtered, washed well with water and dried. Recrystallization from acetonitrile gave 22.5 g of Z-8-bromo-2-(2,2-dimethylcyclopropanecarboxamido)-2-octenoic acid, m.p. 151°–153° C., homogeneous by TLC (4:1 toluene-acetic acid). The NMR spectrum was consistent with the desired structure.

| Anal. ($C_{14}H_{22}BrNO_3$) | Calcd | Found |
| --- | --- | --- |
| C | 50.61 | 50.66 |
| H | 6.67 | 6.96 |
| N | 4.22 | 4.45 |
| Br | 24.05 | 23.95 |

The following ω-bromo compounds were prepared using the same procedure:
Z-6-Bromo-2-(2,2-dimethylcyclopropanecarboxamido)-2-hexenoic acid;
Z-7-Bromo-2-(2,2-dimethylcyclopropanecarboxamido)-2-heptenoic acid.

The compound (+)Z-7-bromo-(2,2-dimethylcyclopropane carboxamido)-2-heptenoic acid, has a melting point of 86°–88° C., and optical rotation,
$[\alpha]_D^{28} = +69.9°$.

EXAMPLE 1

Racemic Z-7-(3-hydroxy-2-pyridylthio)-2-(2,2-dimethyl-cyclopropanecarboxamido)-2-heptenoic acid A solution of 200 mg (0.630 mmole) of Z-7-bromo-2-(2,2-dimethylcyclopropanecarboxamido)-2-heptenoic acid, 72.4 mg (0.57 mmole) of 2-mercapto-3-pyridinol, and 134 mg (1.26 mmole) of $Na_2CO_3$ in 1.0 ml of H O was stirred at room temperature under nitrogen for 3 days.

The reaction mixture was partitioned between 10.0 ml of 1.5 N HCl and 10.0 ml Et$_2$O. The aqueous fraction was adjusted to pH ∼3.5 with 2.5 N NaOH. The product did not oil out, but was extracted into Et$_2$O, dried with MgSO$_4$, and filtered. Concentration of the solution gave 151.0 mg of white crystalline product. This product was recrystallized from nitromethane with several drops of acetic acid, yield 43.0 mg; m.p.=199.0°-200.5° C. and analysis gave for C$_{18}$H$_{23}$N$_2$O$_4$S.0.5 H$_2$O, MW=373.46:

|   | found | calculated |
|---|---|---|
| N | 7.21 | 7.50 |
| C | 58.17 | 57.89 |
| H | 6.72 | 6.75 |
| S | 8.70 | 8.59 |

EXAMPLE 2

(+)-Z-2-(2,2-Dimethylcyclopropanecarboxamido)-7-(3-hydroxy-2-pyridylthio)-2-heptenoic acid A mixture of 2.00 g (6.3 mmole) of (+)-Z-7-bromo-2-(2,2-dimethylcyclopropanecarboxamido)-2-heptenoic acid, 0.73 g (5.75 mmole) of 2-mercapto-3-pyridinol, 1.34 g (12.6 mmole) of Na$_2$CO$_3$, and 8 ml of H$_2$O was stirred at room temperature under N$_2$. After 17.5 hours, the mixture was treated cautiously with 60 ml of 2.5 N HCl (foaming) and shaken with 60 ml of Et$_2$O in a separatory funnel until all of the gummy precipitate obtained initially upon acidification had dissolved in one phase or the other. The aqueous phase was adjusted to pH ∼3-3.5 with 2.5 N NaOH, causing separation of a gum. The mixture was heated on a steam bath, resulting in solidification. After cooling, the solid was collected on a filter and washed with H$_2$O. The air-dried material (1.7 g) was suspended in ∼50 ml of nitromethane, heated on a steam bath, and treated slowly with AcOH while hot until all of the solid dissolved. The solution was treated with charcoal and filtered through Super-Cel. The filtrate was reheated to redissolve crystallized product and then allowed to cool slowly. After standing, the crystallized product was collected on a filter and washed with nitromethane. The material was finally dried in a vacuum oven at 100°. Yield of white crystals=1.24 g (59%, m.p. 188°-189°.

Tlc (2:1 toluene-AcOH) was virtually homogeneous. NMR(DMSO-d$_6$) was consistent with the assigned structure. From the mother liquor there was obtained a second crop of light cream-colored crystals: 0.12 g, m.p. 185°-186°; tlc similar to that of first crop. Total yield of material=1.36 g (65%), ki=0.02; $[\alpha]_D^{27}$=+34.3°.

| Anal. (C$_{18}$H$_{24}$N$_2$O$_4$S) | Calcd. | Found (1st crop) |
|---|---|---|
| C | 59.32 | 59.28 |
| H | 6.64 | 6.58 |
| N | 7.69 | 7.58 |
| S | 8.80 | 8.96 |

EXAMPLE 3

Racemic Z-7-(3-carboxy-2-pyridylthio)-2-(2,2-dimethylcyclopropanecarboxamido)-2-heptenoic acid A solution of 108.0 mg (0.34 mmole) of Z-7-bromo-2-(2,2-dimethylcyclopropanecarboxamide)-2-heptenoic acid, 48.0 mg (0.31 mmole) of 2-mercap-tonicotinic acid, and 72.1 mg (0.68 mmole) of Na$_2$CO$_3$ in 0.5 ml H$_2$O was stirred under N$_2$ at room temperature.

After 1 day, the reaction mixture was partitioned between 2.5 N HCl and Et$_2$O. The product was extracted into 2.5 N HCl and to this layer was added 50% NaOH to pH 2.5-3.0. The product was extracted into Et$_2$O, dried with MgSO$_4$, filtered, and concentrated on the rotovac to yield 51.0 mg (38%) with purity confirmed by NMR and tlc., ki=0.04.

EXAMPLE 4

Racemic Z-7-(5-carboxy-2-pyridylthio)-2-(2,2-dimethylcyclopropanecarboxamido)-2-heptenoic acid A solution of 108.0 mg (0.34 mmole) of Z-7-bromo-2-(2,2-dimethylcyclopropanecarboxamide)-2-heptenoic acid, 48.0 (0.31 mmole) of 6-mercaptonicotinic acid and 72.0 mg (0.68 mmole) of Na$_2$CO$_3$ in 0.5 ml of H$_2$O was stirred under N$_2$ at room temperature.

After 5 days, the reaction mixture was partitioned between 5.0 ml of Et$_2$O and 5.0 ml of 2.5 N HCl. To the aqueous layer was added 10% NaOH until the solution was cloudy white, approx. pH 2-3. The product then extracted into Et$_2$O. The Et$_2$O layer was dried with MgSO$_4$ and concentrated on the rotovac to yield 95.0 mg (71%) of white glassy solid confirmed by NMR, tlc (8:1 toluene:AcOH); m.p. >60° C. (after drying under high vacuum), ki=0.25.

Analysis: C$_{19}$H$_{24}$N$_2$O$_5$S MW=392.47,

|   | Calcd. for 0.25 H$_2$O | found |
|---|---|---|
| C | 57.49 | 57.78 |
| H | 6.22 | 6.42 |
| N | 7.06 | 6.58 |

EXAMPLE 5

(+)-Z-7-(3-carboxy-2-pyridylthio)-2-(2,2-dimethyl cyclopropanecarboxamido)-2-heptenoic acid A solution of 600.0 mg (1.89 mmole) of (+) Z-7-bromo-2-(2,2-dimethylcyclopropanecarboxamido)-2-heptenoic acid, 267.0 mg (1.72 mmole) of 2-mercaptonicotinic acid and 400.6 mg (3.78 mmole) of Na$_2$CO$_3$ in 3.0 ml of H$_2$O was stirred under N$_2$ at room temperature.

After 3 days, the reaction was partitioned between 25.0 ml. of 2.5 N HCl and 25.0 ml of Et$_2$O. The Et$_2$O layer was partitioned with an additional 25.0 ml of 25 N HCl. To the aqueous fractions was added 10% NaOH until the solution turned cloudy white (still pH$\omega$(1.0). Extraction into Et$_2$O, drying with MgSO$_4$, filtration and concentrated on rotovac gave a pale yellow glassy solid, 394.0 mg, m.p. >70° C. Analysis for C$_{19}$H$_{24}$N$_2$O$_5$S MW=392.47

|   | calcd. for 0.25 H$_2$O | found |
|---|---|---|
| C | 57.49 | 57.73 |
| H | 6.22 | 6.55 |
| N | 7.06 | 6.77 |

EXAMPLES 6-13

Using procedures similar to those of Examples 1-5, the following compounds were made, characterized, and tested.

EXAMPLE 6

Z-2-(2,2-dimethylcyclopropanecarboxamido)-6-(3-hydroxy-2-pyridylthio)-2-hexenoic acid; white glassy solid, m.p.=>70° C.; analysis calcd. for $C_{17}H_{22}N_2O_4S.0.25\ H_2O$: C, 57.53; H, 6.39; N, 7.89; found: C, 57.54; H, 6.67; N, 7.93.

EXAMPLE 7

Z-7-(2-pyridylthio)-2-(2,2-dimethylcyclopropanecarboxamido)-2-heptenoic acid; tlc and NMR good.

EXAMPLE 8

Z-7-(4-pyridylthio)-2-(2,2-dimethylcyclopropanecarboxamido)-2-heptenoic acid; a glassy oil; analysis for $C_{18}H_{23}N_2O_4S.\frac{3}{4}\ H_2O$; calc.: C, 59.90; H, 6.76; N, 7.76; found: C, 59.95; H, 6.99; N, 7.01.

EXAMPLE 9

Z-7-(2-carboxyphenylthio)-2-(2,2-dimethyl cyclopropanecarboxamido)-2-heptenoic acid; m.p. 163°-167° C., decomposition; anal. for $C_{20}H_{25}NO_5S.0.75\ H_2O$; calc.: C, 59.32; H, 6.60; N, 3.45; found: C, 59.25; H, 6.36; N, 3.26.

EXAMPLE 10

Z-2-(2,2-dimethylcyclopropanecarboxamido)-7-phenylthio-2-heptenoic acid; m.p. 100°-104° C., dec. anal. for $C_{19}H_{25}NO_3S.0.75\ H_2O$; calc.: C, 63.22; H, 7.40; N, 3.88; found: C, 63.05; H, 7.23; N, 3.90.

EXAMPLE 11

(+)-Z-2-(2,2-dimethylcyclopropanecarboxamido)-8-(3-hydroxy-2-pyridylthio)-2-octenoic acid, a white gummy solid; analysis shows $C_{19}H_{26}N_2O_4S.\frac{1}{2}\ H_2O$.

EXAMPLE 12

Z-8-(1-methyl-5-tetrazolylthio)-2-(2,2-dimethylcyclopropanecarboxamido)-2-octenoic acid; a viscous oil; also made as the t-butyl ester and the sodium salt.

EXAMPLE 13

Z-8-(4-carboxy-6-hydroxy-2-pyrimidinylthio)-2-(2,2-dimethylcyclopropanecarboxamido-2-octenoic acid.

EXAMPLE 14

Z-8-(2-thiazolinylthio)-2-(2,2-dimethylcyclopropanecarboxamido)-2-octenoic acid, m.p. 86°-90° C., ki=0.15, $C_{17}H_{26}N_2O_3S_2$;
calc.: C=55.11; H, 7.07; N=7.56; S=17.31; found: C=54.61; H, 7.20; N=7.36; S=17.21.

What is claimed is:

1. The compound of the following formula:

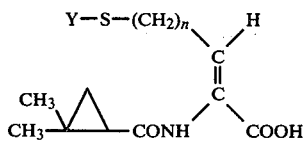

wherein n is an integer from 3-5, Y is pyridyl, pyrimidinyl, tetrazolyl, imidazolyl, thiadiazolyl, thiazinolyl, phenyl, or phenyl having 1 or 2 substituents selected from hydroxyl, oxo, carboxyl, or methyl; and the loweralkyl ($C_{1-6}$) esters and pharmaceutically acceptable salts thereof.

2. The compound of claim 1 wherein Y is pyridyl or phenyl.

3. The compound of claim 2 in which the substituent is hydroxyl or carboxyl.

4. The compound of claim 1 which is Z-7-(3-hydroxy-2-pyridylthio)-2-(2,2-dimethylcyclopropanecarboxamido)-2-heptenoic acid.

5. The racemic (±) form of the compound of claim 4.

6. The S(+) form of the compound of claim 4.

7. The compound of claim 1 which is Z-7-(3-carboxy-2-pyridylthio)-2-(2,2-dimethylcyclopropanecarboxamido)-2-heptenoic acid.

8. The racemic (±) form of the compound of claim 7.

9. The S(+) form of the compound of claim 7.

10. The compound of claim 1 which is Z-(5-carboxy-2-pyridylthio)-2-(2,2-dimethylcyclopropane carboxamido)-2-heptenoic acid.

11. An antibacterial composition comprising an antibacterially effective amount of a combination of thienamycin-type compound and a dipeptidase (E. C. 3. 4. 13. 11) inhibitor which is the compound defined in claim 1, the ratio of the thienamycintype compound to the dipeptidase inhibitor being within the range of about 1:3 to about 30:1.

12. The composition of claim 11, in which the thienamycin-type compound is thienamycin, N-formimidoyl thienamycin, or N-acetimidoyl thienamycin.

* * * * *